US00PP11513P

United States Patent [19]

Carruth

[11] Patent Number: Plant 11,513

[45] Date of Patent: Sep. 19, 2000

[54] FLORIBUNDA ROSE PLANT NAMED 'WEKBIPUHIT'

[75] Inventor: Thomas F. Carruth, Altadena, Calif.

[73] Assignee: Weeks Wholesale Rose Grower, Inc., Upland, Calif.

[21] Appl. No.: 09/198,968

[22] Filed: Nov. 23, 1998

[51] Int. Cl.[7] ..... A01H 5/00

[52] U.S. Cl. ..... Plt./141

[58] Field of Search ..... Plt./141, 138, 149, Plt./150, 151, 102, 108, 140

[56] References Cited

U.S. PATENT DOCUMENTS

P.P. 6,032 10/1987 Nakashima ..... Plt./141
P.P. 11,153 12/1999 Zary ..... Plt./149

*Primary Examiner*—Howard J. Locker
*Attorney, Agent, or Firm*—Christie, Parker & Hale, LLP

[57] ABSTRACT

A new variety of Floribunda rose suitable for garden decoration, having flowers of magenta red coloration.

1 Drawing Sheet

BACKGROUND OF THE INVENTION

This invention relates to a new and distinct variety of Floribunda Rose. The varietal denomination of the new variety is 'WEKbipuhit'. It has as its seed parent the variety known as 'STEbigpu' (U.S. Plant Pat. No. 6,262) and as its pollen parent the variety known as 'HARquantum'.

SUMMARY OF THE INVENTION

Among the features which distinguish the new variety from other presently available and known commercial rose cultivars are the following combination of characteristics: its even magenta flower color, its strong clove fragrance, its cupped flower form, its bright pink styles and its numerous prickles of varying sizes. The plant is a bushy upright to somewhat spreading plant, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'WEKbipuhit' may be asexually propagated by cuttings, budding or grafting.

COMPARISON WITH PARENTS

The new rose may be distinguished from its seed parent, 'STEbigpu' by the following combination of characteristics: whereas 'WEKbipuhit' bears medium size flowers of double petalage, 'STEbigpu' bears significantly larger flowers with more petals. The seed parent is classified as a Hybrid Tea usually bearing one flower per stem, whereas the new rose is classified as a Floribunda usually bearing flowers in clusters.

The new variety may be distinguished from its pollen parent, 'HARquantum' by the following combination of characteristics: whereas 'HARquantum' bears semi-double flowers of magenta coloration with a distinct white eyezone at the center of each flower, 'WEKbipuhit' bears flowers of an even magenta coloration without any eyezone coloration and with significantly more petals. The pollen parent has a very compact moderately short mature habit, whereas the new variety has a significantly taller more spreading mature habit.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of October. Phenotypic expression may vary with environmental, cultural and climatic conditions, as well as differences in conditions of light and soil.

FLOWER

The new variety sometimes bears its flowers singly, but usually in clusters of five or more per stem. Flowers are borne in regular rounded clusters on normal strong short to medium length stems (about 28 to about 42 cms.). Outdoors, the plant blooms very freely and nearly continuously during the growing season. The flowers have a strong clove-like fragrance.

BUD

The peduncle is about 6 to about 9 cms. in length, of slender to average caliper, and usually erect. It is moderately rough, with numerous stipitate glands and some hairs. Peduncle color is between 144A and 146A, sometimes lightly suffused on the side exposed to sun with between 184B and 183D.

Before the calyx breaks, the bud is about 1.2 to about 1.5 cms. in diameter at the widest point, about 1.8 to about 2.2 cms. in length, and pointed to ovoid in shape with a visible hypanthium. The surface of the bud bears some stipitate glands and hairs, usually with slender entire foliaceous parts extending beyond the tip of the bud about ¼ or more of its length. Bud color is between 144A and 146A, sometimes lightly suffused on the side exposed to sun with between 184B and 183D.

The inner surface of the sepals is covered with fine wooly tomentum; sepal margins are lined with few stipitate glands and sometimes with about 1 to about 4 slender foliaceous parts.

As the petals open (after the calyx breaks), the bud is about 1.8 to about 2.4 cms. in diameter at the widest point, about 2.2 to about 2.9 cms. in length, and somewhat pointed to moderately ovoid in form. The color of the under and upper surfaces of the newly opened petals is between 60A and 60C. At the point where the petal attaches, there is a somewhat small zone of near 6C.

BLOOM

When fully open, the bloom ranges from about 6.5 to about 8.5 cms. in diameter. Petalage is double with about 24 to 28 petals and about 1 to 3 petaloids arranged irregularly. When partially open, the bloom form is somewhat cupped to globular, and the petals are somewhat cupped with petal edges sometimes reflexed outward. When fully open, the bloom form is very cupped to globular, and the petals are more loosely cupped to undulated with petal edges sometimes reflexed outward.

PETALS

The substance of the petals is moderately heavy and of medium thickness, with upper surfaces satiny to velvety and under surfaces slightly satiny to shiny. The outer petals are nearly round to broadly obovate in shape with apices somewhat rounded and sometimes slightly notched with one or more notches. The inner petals are more broadly obovate in shape usually with rounded apices.

NEWLY OPENED FLOWER

The under surface of the outer, intermediate and inner petals is between 64C and 53D. The upper surface of the outer, intermediate and inner petals is between 64B and 53C. At the point where the petal attaches, there is a moderately small zone of near 4D.

The general tonality of the newly opened flower is between 64B and 53C.

THREE DAY OLD FLOWER

The under surface of the outer and inner petals is between 68A and 64D. The upper surface of the outer and inner petals is between 67B and 64C. At the point where the petal attaches, there is a moderately small zone of near 155D.

The general tonality of the three day old flower is between 67B and 64C.

On the spent bloom, the petals usually drop off cleanly.

In October in Upland, Calif., blooms on the bush growing outdoors generally last about three to four or more days. Cut roses from plants grown outdoors and kept at normal indoor living temperatures generally last about three to four days.

MALE REPRODUCTIVE ORGANS

Stamens are average in number (approximately 90) and are arranged regularly about the pistils. The filaments are of short to medium length, most with anthers. Filaments are near 4C in color. The anthers are moderately small for the class and all open approximately at the same time. Anther color is near 9B when immature and near 163A at maturity. Pollen is moderately abundant and near 12C in color.

FEMALE REPRODUCTIVE ORGANS

Pistils vary in number (approximately 75). The styles are moderately even, somewhat short to average in length, average in caliper, and somewhat loosely bunched. Stigma color is between 13C and 9B. Style color is between 58C and 54B. Ovaries are usually all enclosed in the calyx.

Hips are of short to average in length, somewhat ovoid to oblong to globular in form, and near 28C in color when ripe. The hip surface is moderately smooth with some stipitate glands and with somewhat thick fleshy walls. The sepals usually drop away. There are approximately 7 to 15 moderately small seeds.

FOLIAGE

The compound leaves are usually comprised of three to five or more leaflets and are borne abundantly. The leaves are about 9.5 to about 12.5 cms. in length and about 7 to about 10 cms. in width at the widest point, moderately heavy in texture, and matte in finish. The terminal leaflets are about 5.5 to about 7.5 cms. in length and about 3.4 to about 4.5 cms. in width at the widest point, oval in shape, with moderately acute apices and round bases. Their margins are usually simply serrate to somewhat irregular.

The upper surface of the mature leaf is between 147A and 137A. The under surface of the mature leaf is between 147B and 148B. The upper surface of the young leaf is between 144A and 146B, usually lightly suffused with between 183C and 184B. The under surface of the young leaf is near 146B, usually heavily suffused with between 183B and 184A.

The rachis is somewhat light to average in caliper and moderately smooth. The upper side is shallowly grooved with few hairs and stipitate glands on the edges of the grooves. The under side of the rachis is moderately smooth with very few stipitate glands and about 1 to 2 very small prickles.

The stipules are about 1.4 to about 1.7 cms. in length and somewhat wide with medium length straight points that usually turn out at an angle of more than 45 degrees and sometimes recurve toward the stem.

The plant displays an above average degree of resistance to powdery mildew and blackspot as compared to other commercial varieties grown under comparable conditions in Upland, Calif.

GROWTH

The plant has a bushy upright to somewhat spreading medium height growth habit (about 90 to about 130 cms. in height and about 80 to about 110 cms. spread at the widest point), with moderately full branching. It displays very vigorous growth and the canes are of moderately heavy caliper for the class.

The color of the major stems is between 146C and 148A. They bear several large prickles that are about 0.8 to about 1.1 cms. in length. The large prickles are almost straight angled very slightly downward with a moderately long broad base; prickle color is between 165B and 164A. The major stem bears numerous small prickles of varying sizes but of similar shape and coloration.

The color of the branches is between 146A and 147A. They bear several large prickles that are of similar size and shape to the large prickles on the major stems; prickle color is between 181A and 179A. The branches bear numerous small prickles of varying sizes but of similar shape and coloration.

The color of the new shoots is between 144A and 146C often moderately suffused with between 183C and 184A. They bear several large prickles that are of similar size and shape to the large prickles on the major stems; prickle color is near 183A. The shoots bear numerous small prickles of varying sizes but of similar shape and coloration.

I claim:

1. A new and distinct Floribunda rose plant of the variety substantially as described and illustrated herein.

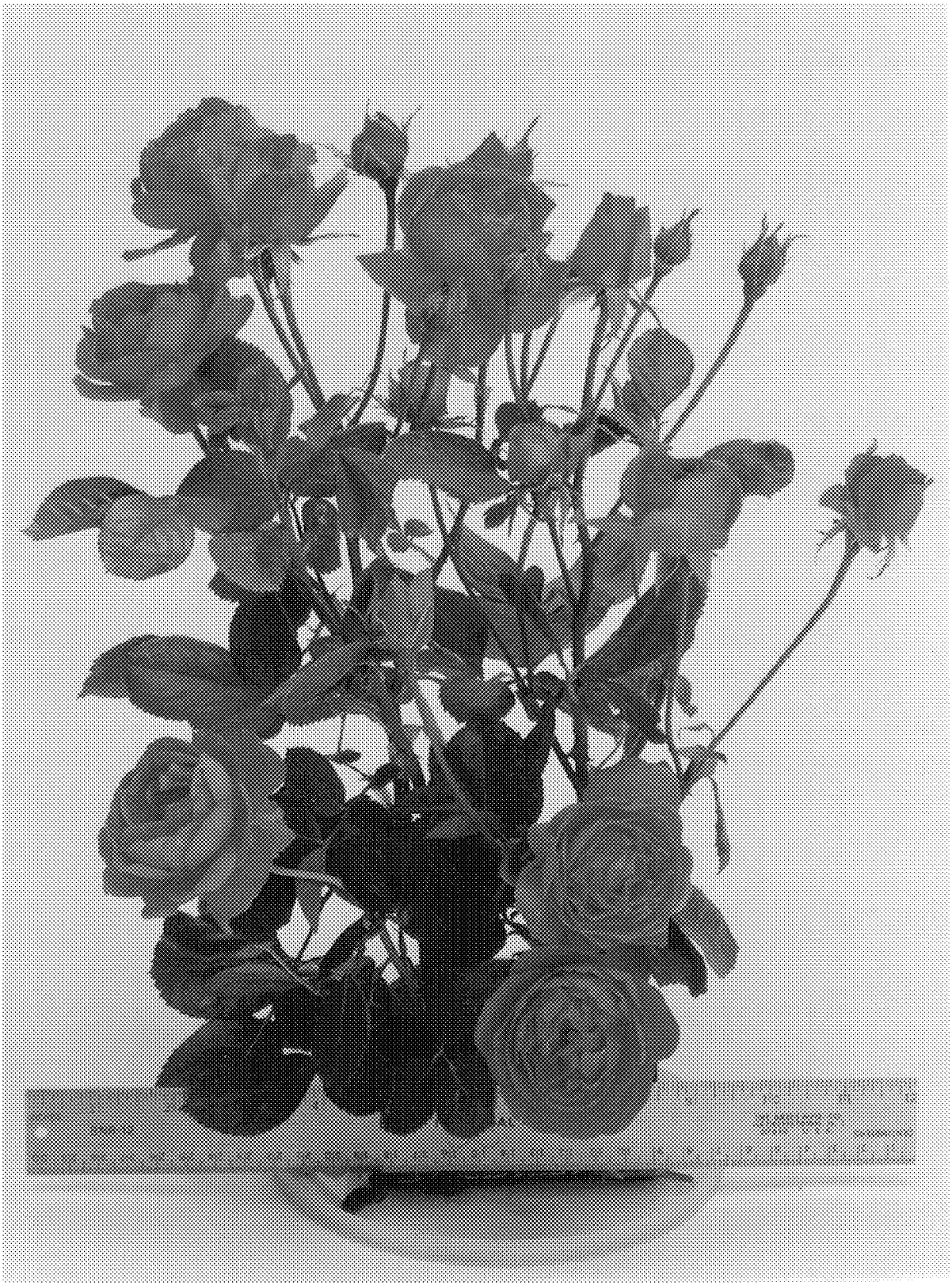

* * * * *